(12) United States Patent
Heacock

(10) Patent No.: US 7,224,822 B2
(45) Date of Patent: May 29, 2007

(54) SYSTEM FOR CAPTURING AN IMAGE OF THE RETINA FOR IDENTIFICATION

(75) Inventor: Gregory L. Heacock, Camas, WA (US)

(73) Assignee: Retinal Technologies, L.L.C., Boston, MA (US)

( * ) Notice: Subject to any disclaimer, the term of this patent is extended or adjusted under 35 U.S.C. 154(b) by 701 days.

(21) Appl. No.: 10/038,168

(22) Filed: Oct. 23, 2001

(65) Prior Publication Data

US 2002/0093645 A1    Jul. 18, 2002

Related U.S. Application Data

(63) Continuation-in-part of application No. 09/704,980, filed on Nov. 2, 2000.

(51) Int. Cl.
*C06K 9/00*    (2006.01)

(52) U.S. Cl. .................................................... 382/117

(58) Field of Classification Search ................ 382/115, 382/117, 155–127; 340/5.53, 5.38; 356/71; 902/3, 6; 713/186, 200; 707/6; 348/78; 351/206, 207; 396/18
See application file for complete search history.

(56) References Cited

U.S. PATENT DOCUMENTS

| | | | |
|---|---|---|---|
| 3,994,597 A * | 11/1976 | Calder et al. ............... 356/251 |
| 4,109,237 A | 8/1978 | Hill |
| 4,227,780 A | 10/1980 | Ohta et al. |
| 4,256,384 A * | 3/1981 | Kani et al. .................. 351/206 |
| 4,393,366 A | 7/1983 | Hill |
| 4,620,318 A | 10/1986 | Hill |
| 4,641,349 A | 2/1987 | Flom et al. |
| D302,153 S | 7/1989 | Karecki |
| 4,975,969 A | 12/1990 | Tal |
| 4,993,068 A | 2/1991 | Piosenka et al. |
| 5,291,560 A | 3/1994 | Daugman |
| 5,297,554 A | 3/1994 | Glynn et al. |
| 5,303,709 A | 4/1994 | Dreher et al. |
| 5,359,669 A | 10/1994 | Shanley et al. |
| 5,412,738 A | 5/1995 | Brunelli et al. |
| 5,442,412 A | 8/1995 | Frey et al. |
| 5,457,747 A | 10/1995 | Drexler et al. |
| 5,499,294 A | 3/1996 | Friedman |
| 5,526,189 A | 6/1996 | Heacock |
| 5,532,771 A | 7/1996 | Johnson et al. |
| 5,572,596 A | 11/1996 | Wildes et al. |
| 5,581,630 A | 12/1996 | Bonneau, Jr. |
| 5,615,277 A | 3/1997 | Hoffman |

(Continued)

FOREIGN PATENT DOCUMENTS

EP    1 003 0369    11/1999

*Primary Examiner*—Matthew C. Bella
*Assistant Examiner*—Tom Y. Lu
(74) *Attorney, Agent, or Firm*—McAndrews, Held & Malloy Ltd.

(57) ABSTRACT

A system for capturing an image of the retina includes an alignment system that aligns the eye along a predetermined axis of the system and at a predetermined distance from the system to illuminate a predetermined area of the retina and to capture an image thereof. The predetermined area of the retina includes the optic disk. The system includes a non-scanned illumination source of red and green light symmetric aspheric lens for a high quality and high contrast image.

38 Claims, 2 Drawing Sheets

U.S. PATENT DOCUMENTS

| | | |
|---|---|---|
| 5,673,097 A | 9/1997 | Heacock |
| 5,751,836 A | 5/1998 | Wildes et al. |
| 5,845,733 A | 12/1998 | Wolfsen |
| 5,861,938 A * | 1/1999 | Heacock ............ 351/218 |
| 5,861,939 A | 1/1999 | Heacock |
| 5,901,238 A | 5/1999 | Matsushita |
| 5,919,132 A | 7/1999 | Faubert et al. |
| 5,956,122 A | 9/1999 | Doster |
| 5,978,494 A | 11/1999 | Zhang |
| 5,995,014 A | 11/1999 | DiMaria |
| 6,148,091 A | 11/2000 | DiMaria |
| 6,247,812 B1 | 6/2001 | Miehle et al. |
| 6,305,804 B1 * | 10/2001 | Rice et al. ............ 351/221 |
| 6,409,341 B1 | 6/2002 | Goldfain et al. |
| 6,490,365 B2 * | 12/2002 | Horiguchi et al. ........ 382/117 |
| 6,594,377 B1 * | 7/2003 | Kim et al. ............ 382/117 |
| 6,690,466 B2 * | 2/2004 | Miller et al. ............ 356/326 |

* cited by examiner

SYSTEM FOR CAPTURING AN IMAGE OF THE RETINA FOR IDENTIFICATION

CROSS-REFERENCE TO RELATED APPLICATIONS

This Application is a continuation-in-part of U.S. patent application Ser. No. 09/704,980 filed Nov. 2, 2000. This application is also related to U.S. patent application Ser. No. 09/705,133 filed Nov. 2, 2000.

STATEMENT REGARDING FEDERALLY SPONSORED RESEARCH OR DEVELOPMENT

N/A

TECHNICAL FIELD

The present invention is directed to a system for capturing an image of an area of the retina containing a pattern unique to an individual for identification.

BACKGROUND OF THE INVENTION

Various devices are known that detect a vascular pattern in a portion of an individual's retina to identify the individual. Examples of such devices are disclosed in U.S. Pat. Nos. 4,109,237; 4,393,366; and 4,620,318. In these devices, a collimated beam of light is focused on a small spot of the retina and the beam is scanned in a circular pattern to generate an analog signal representing the vascular structure of the eye intersecting the circular path of the scanned beam. In the U.S. Pat. No. 4,393,366, the circular pattern is outside of the optic disk or optic nerve and in the U.S. Pat. No. 4,620,318, the light is scanned in a circle centered on the fovea. These systems use the vascular structure outside of the optic disk because it was thought that only this area of the retina contained sufficient information to distinguish one individual from another. The light is scanned in these systems in order to provide sufficient contrast between the vascular structure of the eye outside of the optic disk and the background pigment of the retina. However, systems that use scanners are typically large, complex, expensive and fairly delicate. Moreover, the tilt of the eye can change the retinal structure "seen" by these systems such that two distinct points on the retina can appear to be superimposed. As such, the signal representing the vascular structure of an individual as generated by these systems will vary depending upon the tilt of the eye. This problem is further exacerbated because these systems provide data representing only that vascular structure which intersects the circular path of scanned light, if the individual's eye is not in exactly the same alignment with the system each time it is used, the scanned light can intersect different vascular structures, resulting in a different signal pattern for the same individual. Problems in consistently generating the same signal pattern for an individual make it difficult to use such systems for identification purposes.

Portable systems used by doctors to view the fundus of a patient's eye and capture an image thereof for diagnostic purposes are also known as shown in U.S. Pat. Nos. 5,861,938; 5,861,939 and 5,673,097. These systems scan light using a laser or multiple, sequentially actuated light emitting diodes. However, the image viewed or captured varies with the positioning of the device by the doctor with respect to the patient's eye.

BRIEF SUMMARY OF THE INVENTION

In accordance with the present invention, the disadvantages of prior retinal identification systems have been overcome. The system of the present invention captures an image of a predetermined area of the retina to identify an individual.

More particularly, the system of the present invention includes a source of illumination light. In a preferred embodiment, the source includes one or more light emitting diodes to provide non-scanned light. The system also includes a lens through which the illumination light passes to illuminate the retina wherein the lens also receives light reflected from the retina. An image signal generator is responsive to light reflected from the retina to generate a signal representing an image of an illuminated area of the retina. An alignment system aligns the eye along a predetermined axis of the system and at a predetermined distance from the system so as to illuminate and capture an image of a predetermined area of the retina. In a preferred embodiment, the system is arranged to align the eye so that the centerline of the lens intersects the optic disk.

In one embodiment of the present invention, the alignment system includes an elongated channel having a longitudinal axis at an angle with respect to a centerline of the lens, a light is disposed in the channel at a distance from an end of the channel into which a user looks. A user's eye is aligned along the longitudinal axis of the channel when the light is visible.

The alignment system also includes an ultrasound transducer that is used to determine when the eye is a predetermined distance from the image capturing system. When the eye is at a predetermined distance, the system provides an indication to the user which is visible and/or audible. In a preferred embodiment, the indication is provided by the same light that aligns the eye along the longitudinal axis. When the eye is not at the predetermined distance, the light flashes, the rate of flashing changing as the eye approaches the correct or predetermined distance. Once the eye is at the correct distance, the light stops flashing and remains continuously on as an indication to the user that the eye is properly aligned.

In accordance with another feature of the present invention, the illumination source includes both a red and a green light emitting diode (LED). It has been found that the combination of red and green light provides enhanced contrast between the blood vessels of the retina and the background.

In accordance with a further feature of the present invention, the lens is formed with at least one rotationally symmetric aspheric surface so as to provide a high quality image of the illuminated retinal area.

These and other advantages and novel features of the present invention, as well as details of an illustrated embodiment thereof, will be more fully understood from the following description and drawings.

DETAILED DESCRIPTION OF THE INVENTION

Figure 1:
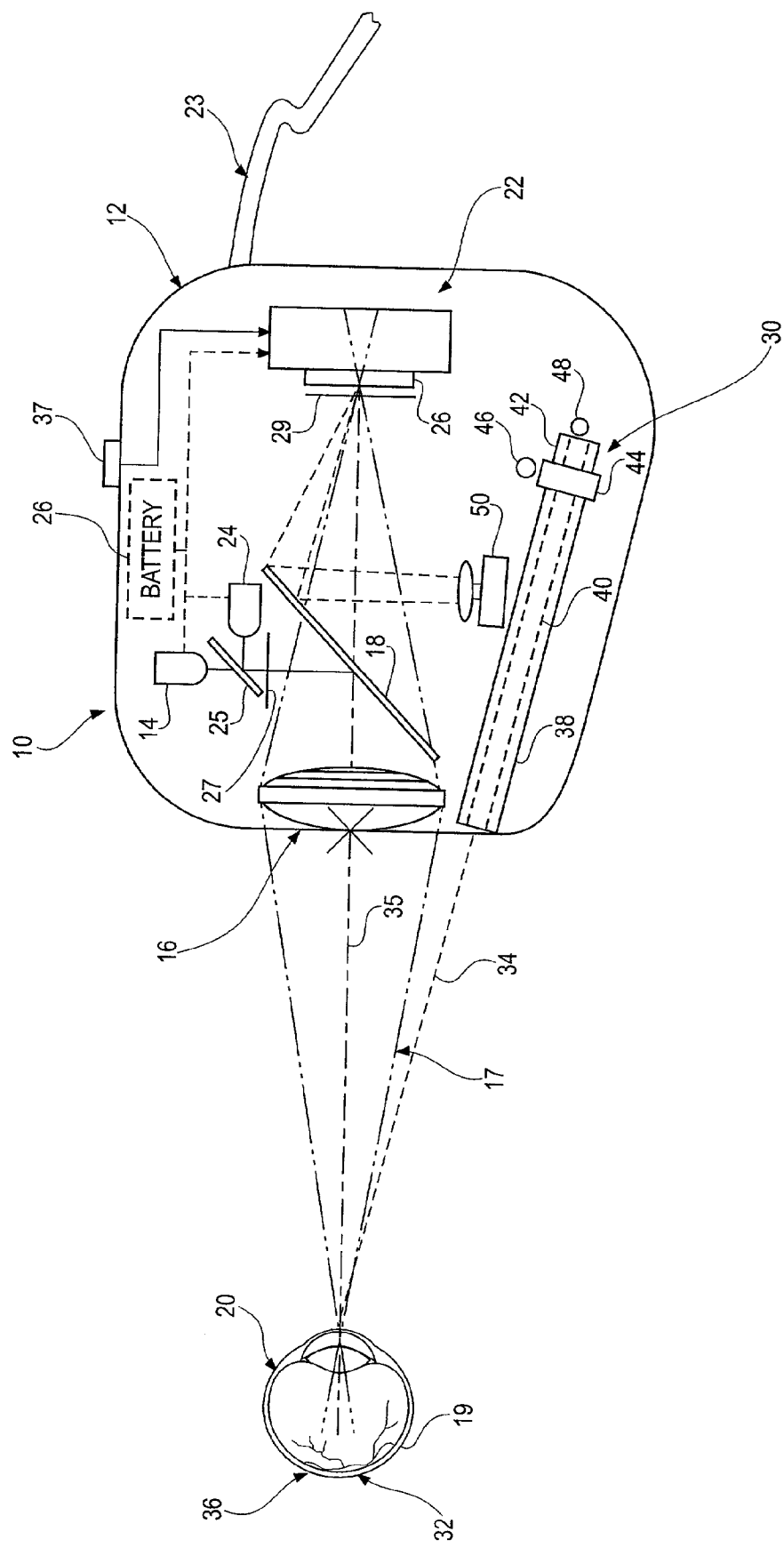
FIG. 1 is a side, cross-sectional view of a first embodiment of a system for capturing an image of an area of the retina for identification in accordance with the present invention.

The system 10 of the present invention captures an image of an area of the retina 19 of an eye 20 and, in particular, an image of the optic disk 32 and surrounding area. It has been found that the optic disk 32 contains the smallest amount of information in the eye to uniquely identify an individual. Because the eye pivots about the optic nerve, an image of the retina centered on the optic disk is the most stable and repeatable image that can be obtained. Further, it has been found that the optic disk can be sufficiently illuminated for image analysis by a non-scanned light source resulting in a system 10 that is considerably less expensive and less complex than prior retinal identification systems. The system 10 of the present invention further has a minimal number of optical components resulting in an extremely compact device that is sufficiently small so as to be contained in a portable and/or hand held housing 12. This feature allows the system 10 of the present invention to be used with portable communication devices including wireless Internet access devices, PALM computers, laptops, etc. as well as standard, personal computers. The system 10 of the present invention provides the captured image to such a device for communication of the image via the Internet or other network to a central location for verification and authentication of the individual's identity. The system of the present invention is also suitable for use at fixed locations. The captured image can be analyzed at the same location at which the image is scanned or at a location remote therefrom.

As shown in FIG. 1, the non-scanned light source of the system 10 includes a light emitting diode (LED) 14 to provide light for illuminating an area of the retina 19 containing the optic disk 32. The light from the LED 14 is directed to the retina 19 by a partially reflecting mirror 18 and an objective lens 16 which determines the image field angle 17. The lens preferably has an effective focal length between 15 and 30 millimeters. In particular, light from the LED 14 is reflected by the mirror 18 through the objective lens 16 to illuminate an area of the retina about a point intersecting a centerline 35 of the lens 16. A target generator 30, discussed in detail below, generates a target that, when viewed by an individual, aligns the eye 20 such that the centerline 35 intersects the optic disk 32. As such, the optic disk 32 is the central retinal structure illuminated by the LED 14. The system 10 can also include a second LED 24 for redundancy. A partially reflective mirror 25 disposed between the LEDs 14 and 24 passes light from the LED 14 therethrough and reflects light from the LED 24 so that the light travels along the same path to illuminate the retina 19.

Light reflected from the illuminated area of the retina 19 is picked up by the objective lens 16. The objective lens 16 directs the light reflected from the retina through the partially reflective mirror 18 to a pin hole lens 26 that is positioned in front of and with respect to the image capturing surface of the CCD camera 22. The pin hole lens 26 ensures that the system 10 has a large depth of focus so as to accommodate a wide range of eye optical powers. The CCD camera 22 captures an image of the light reflected from the illuminated area of the retina and generates a signal representing the captured image. In a preferred embodiment, the center of the CCD camera 22 is generally aligned with the centerline of the lens 16 so that the central, i.e. principal image captured is an individual's optic disk. It is noted that depending upon the type of CCD camera 22 used, the output thereof will be either an analog or digital signal representing the captured image.

Figure 2:
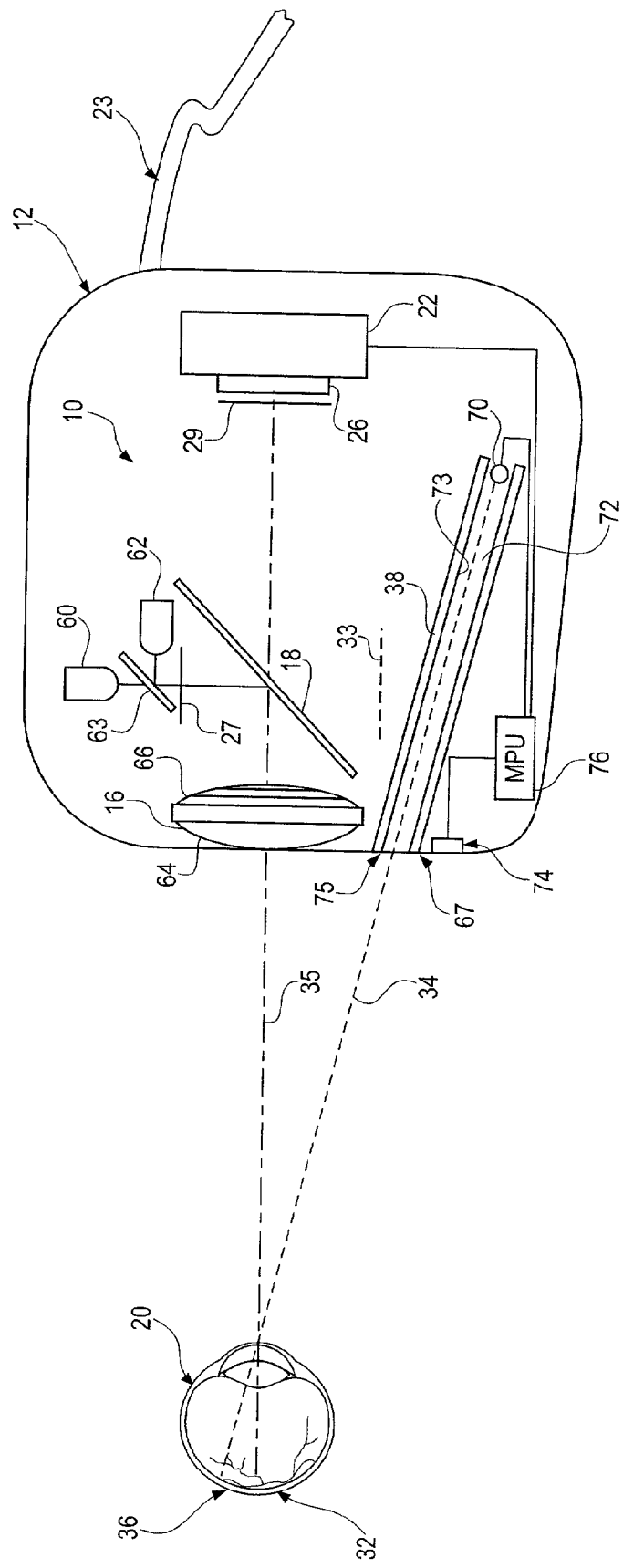
FIG. 2 is a side cross-sectional view of another embodiment of a system for capturing an image of a retina in accordance with the present invention.

In a preferred embodiment, a pair of polarizers 27 and 29 that are cross-polarized are inserted into the optical path of the system to eliminate unwanted reflections that can impair the captured image. More particularly, the polarizer 27 is disposed between the light source 14, 24 and the partially reflecting mirror 18 so as to polarize the light from the source 14, 24 in a first direction. The polarizer 29 is such that it will not pass light polarized in the first direction. As such, the polarizer 29 prevents light from the LEDs 14, 24 from reaching the CCD camera 22. The polarized light from the LEDs 14, 24 becomes randomized as the light passes through the tissues of the eye to the retina so that the light reflected from the retina to the lens 16 is generally unpolarized and will pass through the polarizer 29 to the CCD camera 22. However, any polarized light from the LEDs 14, 24 reflecting off of the cornea 31 of the eye will still be polarized in the first direction and will not pass through the polarizer 29 to the CCD camera 22. Thus, the polarizers 27 and 29 prevent unwanted reflections from the light source 14, 24 and cornea 31 from reaching the CCD camera 22 so that the captured image does not contain bright spots representing unwanted reflections. If desired, a third polarizer 33 as shown in FIG. 2 can be positioned generally parallel to the polarizer 27 but on the opposite side of the partially reflective mirror 18 to eliminate unwanted reflections in that area of the housing as well. This third polarizer may or may not be needed depending on the configuration of the system.

The output of the CCD camera 22 representing the captured image is coupled via a cable 23 to a personal computer, laptop, PALM computer or the like capable of communicating with a remote computer that analyzes the data to identify or authenticate the identity of an individual. It is noted that besides coupling image data out from the CCD camera 22, the cable 23 also preferably provides power to the system 10. Alternately, a battery 26 can be mounted in the housing 12 to provide power to various components of the system 10. Further, the system 10 can include a wireless communication interface such as an IR or RF interface instead of the cable 23 to communicate the captured image data to another device.

The system 10 includes a fixation target generator 30 that generates a fixation target at a predetermined location such that when it is viewed, the optic disk 32 is aligned with the centerline 35 of the objective lens 16. With this alignment, the CCD camera 22 captures an image of the optic disk 32 and immediately adjacent area, with the optic disk 32 being generally centered in the captured image. In order to capture an image of the optic disk, the centerline or longitudinal axis 34 of the target generator 30 is preferably at an angle of approximately 14° with respect to the centerline 35 of the objective lens 16 and CCD camera 22. With such an arrangement, when the eye 20 is aligned with the system 10 such that the individual sees the fixation target, the centerline 34 of the target generator intersects the fovea 36 of the eye 20 and the optic disk 32 is substantially aligned with the centerline 35 of the lens 16 and CCD camera 22. It is noted that because the illumination light is directed to a blind spot on the retina, the optic disk, the illumination light is not irritating to the user. This is opposed to prior retinal identification systems where the bright illumination light is focused on an area of the retina other than the optic disk and is perceived by the user. This bright light can be irritating to the user. As such, the system 10 is more comfortable to use than prior retinal identification systems.

The fixation target generator 30 includes a hollow tube 38 extending along the axis 34. The tube 38 includes a first portion 40 and a second or end portion 42 with a frosted acrylic ring 44 disposed therebetween. A colored LED, for example a green LED 46, is positioned adjacent a sidewall of the ring 44 so that when the LED is illuminated, the frosted ring 44 generates a green disk shaped target. An LED of a second color, for example a red LED 48, is positioned adjacent the end of the tube portion 42 along the centerline 34 so as to generate a red dot target that appears centered in the green disk when the eye 20 is properly aligned with the system 10. In a preferred embodiment, the tube 38 is formed of a black plastic tube so that as an individual looks down the length of the tube he can align his eye so that he is not seeing the inner surface of the tube. The tube 38 is approximately 65 mm in length with a 3 mm inner diameter.

The target generator 30 of the present invention aligns the eye 20 with respect to three perpendicular axes so as to enable the system 10 to consistently capture the same area of the retina 19 for a given individual to enable authentication or identification of the individual via the captured retinal pattern to be more easily accomplished than has heretofore been possible. In order to align the eye 20 with the system 10, the individual looks into the tube 38 and moves the housing 12 towards his eye so that he sees the green disk target. This process aligns the eye 20 along a Z-axis of the target generator 38, wherein the centerline 34 of the target generator 30 extends along the Z-axis. If the red dot appears to the individual to be off center in the green disk, the system 10 is not aligned in the X and/or Y axes. Alignment of the eye 20 with respect to the perpendicular X and Y axes is accomplished by tilting the unit 10 until the individual sees the red dot centered in the green disk. When the individual sees a target comprised of a green disk with a centrally located red dot, the individual's eye 20 is aligned with system 10 with respect to three perpendicular X, Y and Z axes. It is noted, that the unit 10 can include a switch 37 actuable by the individual and coupled to the CCD camera 22. When the individual views the target i.e., red dot centered in the green disk, the individual actuates the switch 37 to signal the CCD camera 22 to capture an image. It should be appreciated that the CCD camera 22, can be controlled to capture an image upon the occurrence of other events indicating alignment of the eye 20 with the device 10 as well.

In a preferred embodiment of the present invention, the system 10 includes a display unit 50 for depicting auxiliary information, an image of which is captured with an image of the illuminated area of the retina. The light from the displayed auxiliary information is passed through a lens 49 to direct the light through the pin hole lens 26. The light from the display unit 50 is reflected to the pin hole lens 26 by the partially reflective mirror 18. The display unit 50 is positioned with respect to the mirror 18 and CCD camera 22 so that an image captured by the CCD camera includes a centrally located image of the illuminated area of the retina combined with an image of the auxiliary information depicted on the display unit 50 wherein the auxiliary information appears in the periphery of the captured image.

The system of the present invention in effect stamps the captured retinal information with auxiliary information to ensure greater security when the image is communicated over a non-secure network such as the Internet. For example, when the digital retinal information is to be transferred to a remote location, the auxiliary information can be used to indicate the time and/or date at which the image was taken. This auxiliary information ensures that the retinal data received at the remote location was currently scanned and is not a stored image being transmitted by someone other than the individual identified by the retinal pattern.

More particularly, the auxiliary display unit 50 depicts information on a display thereof that can be used to authenticate the captured image. In one embodiment, the auxiliary display unit 50 includes an authentication number generator coupled to the display to allow a displayed authentication number to be combined with a retinal image. In a preferred embodiment, the authentication number generator generates a periodically, or non-periodically, changing authentication number so that the number displayed on the unit 50 at any given time is not generally known but known only by the remote authentication system that analyzes the data. Such authentication number generators are known and made, for example, by RSA Security Inc. The RSA SecureID authentication system is capable of generating an authentication number wherein the time at which the number is generated is not apparent from the number itself but can be determined at a remote authentication system. If the remote authentication system determines that the time at which an authentication number marking a retinal image is not within a given period of the time of receipt of the image by the remote authentication system, the remote system will not authenticate the image. In another embodiment, the display unit 50 includes a GPS (Global Positioning Satellite Unit) that receives time and/or date and/or location information for display as auxiliary information. It should be apparent that auxiliary information other than an authentication number, time, date and/or location information can be used to mark the retinal information to provide additional security. It is noted that the auxiliary display is also useable with retinal image capturing devices that use a scanned illumination source as well as the non-scanned system shown.

In accordance with a second embodiment of the system 10 of the present invention as shown in FIG. 2, a red LED 60 and a green LED 62 are simultaneously actuated to illuminate the retina. The light from the red LED 60 and the light from the green LED 62 are combined by a combiner 63 or partially reflected mirror coated so as to pass red light from the red LED 60 and to reflect green light from the green LED 62. It has been found that enhanced contrast between the blood vessels of the retina and the background is achieved by illuminating the retina with light having wavelengths in the red spectrum and the green spectrum.

Further, the objective lens 16 has a first surface 64 and a second surface 66, one or both of which are formed as a rotationally symmetric aspheric surface defined by the following equation.

$$Z = \frac{Cr^2}{1 + \sqrt{1 - (1+k)C^2 r^2}} + A_1 r^2 + A_2 r^4 + A_3 r^6.$$

By forming one or both of the surfaces 64, 66 of the lens 16 as a rotationally symmetric asphere, the quality of the image captured can be substantially increased.

In FIG. 2, an alignment system 67 aligns the eye along a predetermined axis 34 of the system and further aligns the eye so that it is at a predetermined distance from the system. The alignment system 67 includes a member 38 with an elongated channel 72 therein. As shown, the channel 72 is a tubular channel and the member 38 is a tube. It should be appreciated, however that the channel may be formed in a member other than a tube and the channel may have other than a circular cross section. Preferably, the channel 72 is defined by a black inner wall 73 as discussed above. The channel 72 includes an aperture 75 into which a user looks to view a LED 70 that is disposed in the channel 72 at a distance from the aperture 75. The aspect ratio of the diameter of the channel 72 at the location of the LED 70 (or the diameter of the LED 70) to the length of the channel 72 from the aperture 75 to the location of the LED 70 is in a range of 0.02 to 0.084. Preferably, the aspect ratio is 0.04. This aspect ratio can be obtained, for example, by a 0.125 inch diameter LED 70 and a channel length from the aperture 75 to the LED 70 of 3 inches. With an aspect ratio in the given range, the user's eye 20 will be aligned along the longitudinal axis 34 of the channel 72 when the LED 70 is visible. If the eye 20 is not aligned along the longitudinal axis 34, with the given aspect ratio, the LED 70 will not be visible to the user.

The alignment system 67 further includes a transducer 74 such as an ultrasound transducer so as to determine when the eye 20 is at a predetermined distance from the system 10. The ultrasound transducer 74 is positioned adjacent the channel 72 and preferably below the channel 72. The transducer 74 is operated in a transmit and a receive mode. In the transmit mode, the ultrasound transducer 74 generates an ultrasound wave that reflects off of an area of the user's face just below the eye 20, such as the user's cheek. The ultrasound wave reflected off of the user's face is picked up by the transducer 74 in a receive mode. From the time at which the wave is sent, the time at which the wave is received, and the speed of the wave through air, the distance between the system 10 and the eye 20 can be determined by a microprocessor 76 or a dedicated integrated circuit (I.C.). The microprocessor 76 or I.C. compares the determined distance between the eye 20 and the system 10 to a predetermined distance value stored in a memory, register or the like, accessible by the microprocessor 76 or I.C. When the user's eye 20 is not at the desired distance from the system 10, the microprocessor 76 controls the LED 70 to flash. As the eye 20 approaches the correct distance, the rate of flashing of the LED 70 can change, for example the rate can increase, so as to advise the user that the eye is approaching the desired distance from the system. When the microprocessor 76 determines from the output of the ultrasound transducer 74 that the eye 20 is at the predetermined or correct distance, the microprocessor 76 controls the LED 70 so that it stops flashing and is on continuously as long as the user's eye 20 is at the correct distance from the system 10. When the microprocessor 76 determines that the eye is at the correct position, the microprocessor signals the CCD camera 22 to actuate the camera to capture an image of an area of the properly aligned retina.

In this embodiment, the single LED 70 provides an indication to the user that the eye 20 is correctly aligned along the longitudinal axis 34 and is at a desired distance from the system 10. It should be appreciated however, that instead of flashing the LED 70, or in addition thereto, an audible tone can be provided to indicate that the eye is not at the correct position, approaching the correct position, and/or is at the correct position by changing the frequency or nature of the tone, etc. Further, visual indications other than a single LED 70 can also be used to indicate proper positioning with respect to the system 10.

As discussed above, the longitudinal axis 34 of the alignment system is preferably at an angle of approximately 14° from the centerline of the lens 16 so that when the eye 20 sees the LED 70, the optic disk 32 is aligned with the centerline 35 of the lens 16 and the CCD camera 22. This system allows the CCD camera 22 to repeatably capture an image of the optic disk 32 and surrounding area for identification purposes. It should be appreciated, however, that the alignment system 67 can also be used to capture images of other areas of the eye as well.

Further, the red and green illumination lights 60 and 62 may be simultaneously turned on before alignment of the eye is determined. However, because the eye is more sensitive to green light, actuation of the green LED 62 may be delayed until the microprocessor 76 determines that the eye is in the correct position. In this embodiment, when the microprocessor 76 determines that the eye is in the correct position, the microprocessor would turn on the green illumination light 62 immediately before signaling the CCD camera 22 to capture the image of the illuminated retina so as to minimize the time that any potentially irritating light is directed into the eye. The red illumination LED 62 can be turned on prior to turning on the green LED because red light is generally not perceived as irritating. Alternatively, the red light can be turned on at the same time as the green light is turned on by the microprocessor 76 or I.C., that is, when the eye is determined to be in the correct position and before signaling the CCD camera 22 to capture the image.

The optical arrangement of the present invention enables the system 10 to be extremely compact for mounting in a hand/held and/or portable housing 12. For example, the housing 12 as shown in FIG. 1 has a length, a width and a height that is less than 4 inches. Although the portability of the system 10 enables the retinal identification system of the present invention to be used in applications heretofore not possible, the system 10 can be mounted at a fixed location as well. Moreover, the system's own microprocessor 76 can authenticate the identity of an individual. In such an embodiment, the microprocessor 76 can receive data representing an image of an individual's retina and/or optic disk from a remote location or from an identification card encoded with the data and input to the system 10 for comparison by the microprocessor 76 to the image data captured by the system 10 from the illuminated retina. If the microprocessor 76 determines a match, the identity of the individual is authenticated. In such an embodiment, the microprocessor 76 preferably operates in accordance with the method described in U.S. patent application Ser. No. 09/705,133 filed Nov. 2, 2000 and incorporated herein by reference. Many other modifications and variations of the present invention are possible in light of the above teachings. Thus, it is to be understood that, within the scope of the appended claims, the invention may be practiced otherwise than as described hereinabove.

What is claimed and desired to be secured by Letters Patent is:

1. A system for capturing an image of a retina of an eye for identification comprising:

a source of illumination light;

a lens through which the illumination light passes to illuminate the retina, the lens receiving light reflected from the retina;

an image signal generator responsive to light reflected from the retina to generate a signal representing an image of an illuminated area of the retina; and an alignment system to align the eye along an axis that is at a predetermined angle with respect to a centerline of the lens, the alignment system including an elongated straight channel having an end into which a user looks, the longitudinal axis of the channel being the axis along which the eye is aligned and an object being disposed in the channel at a distance from the end into which the user looks wherein the aspect ratio of the diameter of the channel to the length of the channel from the location of the object to the end into which the user looks is such that the object is viewable when the eye is aligned along the longitudinal axis and is not viewable when the eye is not aligned along the longitudinal axis, and the system including an ultrasound transducer, and the system being responsive to the transducer to determine when the eye is at a predetermined distance from the image capturing system and providing an indication to the user when the eye is at the predetermined distance.

2. A system for capturing an image of a retina of an eye for identification as recited in claim 1 wherein said object is a light.

3. A system for capturing an image of a retina of an eye for identification as recited in claim 1 wherein the object is a light, the light is flashing when the eye is not at the predetermined distance, the flashing rate of the light changing as the distance of the eye approaches the predetermined distance and the flashing stopping when the eye is at the predetermined distance.

4. A system for capturing an image of a retina of an eye for identification as recited in claim 1 wherein the object is a light and the aspect ratio of the diameter of the channel at the location of the light to the length of the channel from the end into which the user looks to the location of the light is in a range of 0.02 to 0.084.

5. A system for capturing an image of a retina of an eye for identification as recited in claim 1 wherein the object is a light and the aspect ratio of the diameter of the channel at the location of the light to the length of the channel from the end into which the user looks to the light is approximately 0.04.

6. A system for capturing an image of a retina of an eye for identification as recited in claim 1 wherein the angle is such as to illuminate the optic disk to generate a signal representing an image thereof.

7. The system for capturing an image of a retina of an eye for identification as recited in claim 1 wherein said indication is visual.

8. A system for capturing an image of a retina of an eye for identification as recited in claim 1 wherein the said indication is audible.

9. A system for capturing an image of a retina of an eye for identification as recited in claim 1 wherein the illumination source is a non-scanned light source.

10. A system for capturing an image of a retina of an eye for identification as recited in claim 1 wherein the illumination source includes a green light and a red light.

11. A system for capturing an image of a retina of an eye for identification as recited in claim 10 wherein the lights are light emitting diodes.

12. A system for capturing an image of a retina of an eye for identification as recited in claim 1 wherein said lens has at least one rotationally symmetric aspheric surface.

13. A system for capturing an image of a retina of an eye for identification as recited in claim 1 wherein said image signal generator is a CCD camera.

14. A system for capturing an image of a retina of an eye for identification as recited in claim 1 including a pinhole lens disposed between the image signal generator and the lens.

15. A system for capturing an image of a retina of an eye for identification comprising:
a source of illumination light;
a lens through which the illumination light passes to illuminate the retina, the lens receiving light reflected from the retina;
an image signal generator responsive to light reflected from the retina to generate a signal representing an image of an illuminated area of the retina; and
an alignment system including a member with an elongated straight channel therein, the channel having an end into which a user looks and a longitudinal axis at an angle with respect to a centerline of the lens, the angle being selected such that when the eye is aligned along said axis, said centerline intersects an area of the retina other than the fovea and an object disposed in the channel at a distance from the end into which the user looks wherein the aspect ratio of the diameter of the channel to the length of the channel from the location of the object to the end into which the user looks is such that the object is viewable when the eye is aligned along the longitudinal axis and is not viewable when the eye is not aligned along the longitudinal axis.

16. A system for capturing an image of a retina of an eye for identification as recited in claim 15 wherein said object is a light.

17. A system for capturing an image of a retina of an eye for identification as recited in claim 16 including an ultrasound transducer for determining when the eye is at a predetermined distance from the image capturing system and wherein the light is flashing when the eye is not at the predetermined distance, the flashing rate of the light changing as the distance of the eye approaches the predetermined distance and the flashing stopping when the eye is at the predetermined distance.

18. A system for capturing an image of a retina of an eye for identification as recited in claim 15 wherein the object is a light and the aspect ratio of the diameter of the channel at the location of the light to the length of the channel from the end into which the user looks to the location of the light is in a range of 0.02 to 0.084.

19. A system for capturing an image of a retina of an eye for identification as recited in claim 15 wherein the object is a light and the aspect ratio of the diameter of the channel at the location of the light to the length of the channel from the end into which the user looks to the light is approximately 0.04.

20. A system for capturing an image of a retina of an eye for identification as recited in claim 15 wherein the channel is a tubular channel with a black channel wall.

21. A system for capturing an image of a retina of an eye for identification as recited in claim 15 wherein the alignment system determines when the eye is a predetermined distance from the image capturing system.

22. A system for capturing an image of a retina of an eye for identification as recited in claim 21 including an ultrasound transducer.

23. A system for capturing an image of a retina of an eye for identification as recited in claim 21 wherein the object is a light that is viewable when the eye is aligned along the longitudinal axis and the light has at least a first state and a second state, the light changing state when the eye is a predetermined distance from the image capturing system.

24. A system for capturing an image of a retina of an eye for identification as recited in claim 15 wherein the illumination source is a non-scanned light source.

25. A system for capturing an image of a retina of an eye for identification as recited in claim 15 wherein the illumination source includes a green light and a red light.

26. A system for capturing an image of a retina of an eye for identification as recited in claim 25 wherein the lights are light emitting diodes.

27. A system for capturing an image of a retina of an eye for identification as recited in claim 15 wherein said lens has at least one rotationally symmetric aspheric surface.

28. A system for capturing an image of a retina of an eye for identification as recited in claim 15 wherein said image signal generator is a CCD camera.

29. A system for capturing an image of a retina of an eye for identification comprising:
   a source of illumination light;
   a lens through which the illumination light passes to illuminate the retina, the lens receiving light reflected from the retina;
   an image signal generator responsive to light reflected from the retina to generate a signal representing an image of an illuminated area of the retina; and
   an alignment system including:
      an elongated channel having an end into which a user looks and a longitudinal axis at an angle with respect to a centerline of the lens;
      a light disposed in the channel at a distance from the end into which a user looks so that the user's eye is aligned along the longitudinal axis when the light is visible, the light having at least a first state and a second state; and
      a distance detector to determine when the eye is a predetermined distance from the image capturing system, the light changing state when the eye is at the predetermined distance.

30. A system for capturing an image of a retina of an eye for identification as recited in claim 29 wherein the light is flashing in one state and the light is continuously on in another state.

31. A system for capturing an image of a retina of an eye for identification as recited in claim 29 wherein the light is in a flashing state when the eye is not at the predetermined distance and the light is continuously on when the eye is at the predetermined distance.

32. A system for capturing an image of a retina of an eye for identification as recited in claim 31 wherein the flashing rate changes as the eye approaches the predetermined distance.

33. A system for capturing an image of a retina of an eye for identification as recited in claim 29 wherein the channel is a tubular channel with a black channel wall.

34. A system for capturing an image of a retina of an eye for identification as recited in claim 29 wherein the distance detector includes an ultrasound transducer.

35. A system for capturing an image of a retina of an eye for identification as recited in claim 29 wherein the ultrasound transducer is adjacent the channel.

36. A system for capturing an image of a retina of an eye for identification as recited in claim 29 wherein the object is a light and the aspect ratio of the diameter of the channel at the location of the light to the length of the channel from the end into which the user looks to the location of the light is in a range of 0.02 to 0.084.

37. A system for capturing an image of a retina of an eye for identification as recited in claim 29 wherein the object is a light and the aspect ratio of the diameter of the channel at the location of the light to the length of the channel from the end into which the user looks to the light is approximately 0.04.

38. A system for capturing an image of a retina of an eye for identification as recited in claim 29 wherein the angle is such as to illuminate the optic disk to generate a signal representing an image thereof.

* * * * *